United States Patent [19]

Pert et al.

[11] 4,073,885

[45] Feb. 14, 1978

[54] ANODYNIN, AN ENDOGENOUS OPIATE ANALGESIC FROM HUMAN BLOOD, AND PROCESS FOR RECOVERING SAME

[75] Inventors: Candace B. Pert; Agu Pert, both of Bethesda, Md.; John F. Tallman, Washington, D.C.

[73] Assignee: The United States of America as represented by the Department of Health, Education and Welfare, Washington, D.C.

[21] Appl. No.: 722,207

[22] Filed: Sept. 10, 1976

[51] Int. Cl.² .................... A61K 35/14; A61K 37/00
[52] U.S. Cl. .................................... 424/101; 424/177
[58] Field of Search .............................. 424/101, 177

[56] References Cited

PUBLICATIONS

Pert et al., Proc. Natl. Acad. Sci. U.S.A., 73 (1976).
Pert et al., Brain Research, 70:184–188 (1974).
Pert et al., Science, 179:1011–1014 (1733).
Pert, "The Opiats Receptor", *Cell Membrane Receptors for Viruses, Antigens and Antibodies, Polypeptide Hormones, and Small Molecules,* ed. by Beers and Bassett, Raven Press, New York, 1976 pp. 435–450.

*Primary Examiner*—Stanley J. Friedman
*Attorney, Agent, or Firm*—John S. Roberts, Jr.; Norman J. Latker; Thomas G. Ferris

[57] ABSTRACT

A method of recovering a hormone from human blood plasma which has morphine agonist properties which comprises heating said plasma, extracting into butanol to recover anodynin, and purifying said anodynin by centrifuging and ion exchange column separation. Anodynin has a molecular weight of about 600.

3 Claims, No Drawings

ANODYNIN, AN ENDOGENOUS OPIATE ANALGESIC FROM HUMAN BLOOD, AND PROCESS FOR RECOVERING SAME

This invention relates to the recovery of a previously unrecognized hormone from human plasma. This substance has been found to give profound long-lasting analgesia even in microgram amounts and may also be characterized as a hormone circulating in human blood which possesses morphine-like physiological effects. It has certain obvious advantages to synthetic analgesic substances in that it is a natural substance which is tolerated in the human body and is not subject to immunological rejection.

The general modus of recovery is from human plasma by heating, extracting into butanol, and purifying by molecular sieve chromatography an anion exchange, leading to a highly purified anodynin preparation. The name anodynin, which was chosen for this substance, is derived from anodyn (Greek, anodynos) which means a drug tha calms and allays pain.

When this substance, termed anodynin, is microinjected into rat periaqueductal gray matter, it causes a profound long-lasting analgesia which is prevented by prior injection of the opiate antagonist naloxone.

PRIOR ART

The prior art picture into which the present application fits is of recent origin.

A. Prior Art by the Inventor(s)

Pert et al., "Isolation of a Novel Endogenous Opiate Analgesic from Human Blood," *Proc. Natl. Acad. Sci. USA*, 73(July 1976).

Pert, "The Opiate Receptor," *Cell Membrane Receptors for Viruses, Antigens and Antibodies, Polypeptide Hormones, and Small Molecules*, edited by Beers and Bassett, Raven Press, New York, 1976, pages 435–450.

Pert et al., "Localization of Opiate Receptor Binding in Synaptic Membranes of Rat Brain," *Brain Research*, 70:184–188 (1974).

Pert et al., "Opiate Receptor: Demonstration in Nervous Tissue," *Science*, 179:1011–1014 (1973).

B. Prior Art by Others

Cox et al., "A Peptide-Like Substance from Pituitary that Acts Like Morphone 2, Purification and Properties," *The Opiate Narcotics, Neurochemical Mechanism in Analgesia and Dependence*, Pergamon Press, New York, 1975, pages 25–30.

Hughes et al., "Identification of Two Related Pentapeptides From the Brain with Potent Opiate Agonist Activity," *Nature*, 258:577–579 (Dec 18, 1975). This article identifies enkephalin, a natural ligand for opiaate receptors, as being composed of the pentapeptides H-Tyr-Gly-Gly-Phe-Met-OH and H-Tyr-Gly-Gly-Phe-Leu-OH.

In Section A above, the Pert prior art literature articles relate generally to the opiate receptor concept which teaches that opiate receptor binding is stereospecific and that a class of opiates which activates or keys to the opiate receptors in the brain is similar in structure to morphine. It is surprising that the present structures of peptide-type generalized structure should also mimic the activity of morphine.

In the above prior art, the Cox et at. article is devoted to the discussion of a peptide-like opioid in bovine and porcine pituitary.

Hughes et al. have isolated two pentapeptides from procine brain on the basis of their morphine-like effects on the mouse vas deferens and guinea pig ileum. The Hughes development of enkephalin from bovine brain is distinguishable from the present anodynin and will be discussed post.

In the action of anodynin in animals, it has been shown that this small peptide has a high affinity for opiate receptors in vitro and produces lasting analgesia and sedation in rats. It has further been found that in experimenting with rats, anodynin is connected in some way with the mechanism of action of the pituitary gland. Since this opiate receptor binding material is found to be less than 5% in serum from hypophysectomized rats. Thus, since hypophysectomy almost completely abolishes blood anodynin, it is concluded that anodynin is stored in and released from the pituitary in the manner of classical hormones, or that a pituitary factor is required for its maintenance.

Opiate receptors are hypothetical sterospecific tissue constituents with which morphine and other opiate agonists complex to initiate their pharmacological effects. The rather strict structural requirements for opiate activity such as morphine-like drugs have suggested to some investigators that opiate receptors normally interact with some naturally occurring endogenous ligand for which morphine and its congeners provide structural analogues.

The endogenous ligand located in the central nervous system might also function as a neuromodulator or a neuro-transmitter for which the opiate receptor is a post-synaptic recognition unit which alters sodium ion conductance. An additional function has been proposed in the prior art and the suggestion has been made that the endogenous ligand may be stored and released from pituitary and act at remote opiate-sensitive tissues in the manner of a typical pituitary hormone.

After purification, molecular weight determination of the present blood inhibitory substance indicates a molecular weight of about 600.

DIFFERENCES BETWEEN ANODYNIN AND ENKEPHALIN

While anodynin may be a close structural analog to enkephalin, it differs from it in its sensitivity to brain enzymatic degradation, its duration of analgesia, and its thin-layer mobility in three solvent systems. It has been shown by Chang et al, "Opiate Receptor Affinities and Behavioral Effects of Enkephalin: Structure-activity Relationship of Ten Synthetic Peptide Analogues," *Life Science*, in press, that enkephalin, which is rapidly destroyed in the brain, requires doses at least 40 times higher than morphine to elicit analgesia, which disappears completely 1–2 minutes after micro-injection. By contrast, anodynin appears to be relatively resistant to inactivation by brain enzymes in vitro and elicts naloxone-reversible analgesia which is, at low doses, only slightly diminished 1 hour after micro-injection. In any case, it is highly unlikely that anodynin is a degradation product of enkephalin or vice versa, since neither substance gives evidence of the generation of the other upon repeated thin-layer chromatographic analysis and storage.

METHOD

Anodynin may be recovered and purified from human plasma preferably which has been refrigerated for several weeks after removal of blood cells. The plasma which was in batches of 1 liter, was acidified to pH 3 with HCl in a boiling water bath with the resultant precipitate removed by low-speed centrifugation. After a pH adjustment to about 9.0 by Tris base (tris propanol amine), the supernatant fluid and the precipitate material were each extracted twice with half volumes of water-saturated butanol. The clear yellow butanol extract is evaporated to dryness at 22° C and the resulting residue was dissolved in 50-100 ml of tris HCl buffer (0.05 M, pH 7.7 at 25°). After removal of undissolved material by low-speed centrifugation, the extract was applied to a column containing Dowex 1-X8 anion exchange resin in the chloride form (styrene-DVB resin, Baker Chemicals) and washed with Tris buffer (0.05 M, pH 7.0 at 25°) until the effluent became colorless (about 200 ml). The resin was lyophilized and subsequently again dissolved in Tris buffer at pH 7.4 at 37° and 0.1 M and filtered through a milipore filter and subsequently to a column containing Bio-Gel P-2 (molecular sieve chromatography gel; BioRad Corp., San Francisco, Calif.).

EXAMPLE

A. Materials and Methods

Preparation from Human Blood

Outdated human plasma, which had been refrigerated for several weeks after removal of blood cells by centrifugation at 600 × g, was obtained from the National Institutes of Health Blood Bank. Batches of about 1 liter were adjusted to pH 3 with HCl and heated in a boiling-water bath, and the resultant precipitate was removed by low-speed centrifugation. After pH adjustment to 9.0 by Tris base, the supernatant fluid and precipitate were each extracted twice with approximately half volumes of water-saturated butanol. The clear yellow butanol extract was evaporated to dryness at 22° on a rotary evaporator. The resultant residue was dissolved in 50-100 ml of Tris-HCl buffer (0.05 M, pH 7.7 at 25°). After removal of undissolved material by low-speed centrifugation, the extract was applied to a column (20 × 4 cm) containing Dowex 1-X8 anion exchange resin (chloride form) (Baker Chemicals) and washed with Tris buffer (0.05 M, pH 7.0 at 25°) until the effluent became colorless (about 200 ml). The resin was eluted batchwise by mixing it in an equivalent volume of glycine-HCl buffer, pH 3.0. After lyophilization, the white residue was dissolved in 10-20 ml of Tris buffer (pH 7.4 at 37°, 0.1 M) and filtered through a Millipore filter (45 $\mu$m size) before application to a 80 × 5 cm column containing Bio-Gel P-2. The column was eluted with 2 liters of the same buffer at a flow rate of 50 ml/hr, and 15 ml fractions were collected and assayed for opiate receptor activity. The pooled fractions containing the opiate receptor inhibitory activity were lyophilized, dissolved in distilled water, reextracted into butanol, dried, and dissolved in distilled water for behavioral analysis, Tris buffer for opiate receptor studies, or methanol for thin-layer analysis.

Thin-Layer Analysis

The redissolved anodynin was applied to a silica gel G plate (0.25 mm thick, Brinkman Instruments) which had been activated at 100° for 1 hr. The plate was developed in a solvent system of chloroform, methanol, 20% ammonia (60:30:5, vol/vol/vol), and dried in air, and the lanes were visualized by brief exposure to iodine vapor. Each spot was scraped from the plate, eluted with chloroform and methanol (1:1, vol/vol), and dried under nitrogen.

Opiate Receptor Assay

Opiate receptor binding was assayed by rapid filtration, as described in Pert and Snyder, "Opiate Receptor: Demonstration in Nervous Tissue," *Science*, 179:1011-1014, with minor modifications. Male rats weighing 180-220 g (Sprangue-Dawley) were decapitated and each brain with the cerebellum removed was homogenized in 150 ml of ice-cold standard buffer (0.05 M Tris-HCl, ph 7.4 at 37°). After centrifugation at 4° at 12,000 × g, the membranes were reconstituted in standard buffer. After recentrifugation, each brain was suspended in 10 ml of the standard buffer.

Aliquots of the freshly prepared membrane preparation (100 $\mu$l) were incubated for 1 hr at 0° with 100 mM NaCl in a final volume of 0.5 ml with [$^3$H]naloxone (Amersham-Searle, 34 Ci/mmol) in a concentration of 1.3 nM (20,000 cpm). After rapid filtration and washing with two 7-ml portions of ice-cold standard buffer, membrane-laden filters were transferred and counted at 40-45% efficiency at least 6 hours after shaking with detergent scintillation fluor (Aquasol, New England Nuclear). Control incubations containing levallorpham (100 nM) or dextrallorphan (100 nM), which did not significantly reduce binding, were included. Stereospecific binding represented 80-90% of the total bound naloxone in all experiments.

Assay of Rat Blood Samples

Rats were killed by decapitation and blood was collected. One milliliter of serum from each rat was obtained by centrifugation at 40,000 × g for 10 min. Serum was adjusted to pH 3 with HCl, heated briefly in a boiling water bath, and extracted into 2 ml of water-saturated butanol after pH adjustment to 9.0 with Tris buffer. After evaporation (Evapo-Mix, Buchler Instruments), samples were reconstituted in 1 ml of standard Tris buffer and aliquots were assayed for opiate receptor inhibitory activity.

Hypophysectomized Rats

Hypophysectomized male rats weighing 150 g and sham-operated controls were purchased from Hormone Assay, Chicago. Pituitaries were aspirated after parapharangeal entry into tracheotomized rats under light ether anesthesia. Sham-operated rats had identical manipulation with the exception of aspiration. One week after surgery, hypophysectomized and control rats were alternately killed by decapitation and their serum was collected, extracted, and assayed for opiate receptor inhibitory activity.

Assessment of Analgesia

Eight rats were stereotaxically implanted with chronic indwelling cannulae guides constructed from 23 gauge TW stainless steel tubing. The cannulae tips were aimed for an area 2 mm dorsal to the periaqueductal gray matter (AP + 0.6, Lat + 0.5, DV + 3.0, in the coordinates of Pellegrino et al., in *A Stereotaxic Atlas of the Rat Brain*, Appleton-Century-Crofts, New York, 1967), an area which has been shown to be critical for mediating the analgetic actions of opiates (Jacquet et al., "Morphine Action at Central Nervous System Sites in Rat: Analgesia or Hyperalgesia Depending on Site and Dose," *Science*, 182,490-492; and Pert et al., "Sites of Morphine Induced Analgesia in the Primate Brain: Relation to Pain Pathways," *Brain Res.*, 80, 135-140). Testing was initiated approximately 1 week following surgery. The antinociceptive actions of morphine and anodynin were assessed using a modification of the D'Armour and Smith paradigm in which the latency for a rat to remove its tail from under a radiant heat source is measured in seconds. Baseline "tail-flick" latencies were always determined approximately 30 minutes prior to a drug or control injection by four trials separated by 10 sec. A trial was automatically terminated if an animal failed to remove its tail within 12 seconds.

All animals received the following drugs and drug combinations in a counterbalanced order separated by 5 days; 4 $\mu$l of anodynin, 4 $\mu$l of anodynin + 20 mg/kg of naloxone 15 min. prior, 4 $\mu$l of 1.25 $\mu$g/$\mu$l of morphine sulfate + 20 mg/kg of naloxone 15 min. prior, and 4 $\mu$l of sterile water (vehicle for morphine). The solutions were injected into the central gray matter with 30 guage injectors which extended 2 mm past the tip of the guide cannula. The injection rate was 15 $\mu$l/min. Testing for antinociception was initiated immediately after an injection. Animals were tested at 1-min. intervals for 5 min. and then at 10, 15, 30, and 60 min. At the end of the study, all animals were sacrificed and their brains were prepared following standard histological procedures to localize cannulae placements.

B. Results

Purification

The major purification step is the efficient extraction into butanol, which removes most protein and yields a lipid-rich fraction.

Properties

The ability of the blood inhibitory factor eluted from the thin-layer plate to be degraded by enzymes present in brain was examined by incubating the blood substance with membranes or supernatant fluid from rat brain, terminating the enzyme action by boiling, and subsequently adding the product to the opiate receptor assay (see Table 1). The blood substance appeared to be relatively resistant to loss of inhibitory activity. By contrast, enkephalin inhibition of opiate receptor binding was completely and rapidly reversed by brain enzymatic activity.

The blood inhibitory factor inhibits opiate receptor binding of [$^3$H]naloxone with a slope that is not significantly different from that of morphine and other opiates.

Behavioral Effects

Anodynin produced an immediate, profound, long-lasting analgesia as assessed by the rat "tail-flick" test. Four microliters, containing sufficient analgetic activity to cause approximately 20% inhibition in the opiate receptor assay, caused an increased in tail-flick latency equivalent to that produced by a total of 5 $\mu$g of morphine sulfate in 4 $\mu$l of water. The antinociceptive actions of morphine as well as anodynin were blocked by pretreatment with 20 mg/kg of the opiate antagonist naloxone injection intraperitoneally. A repeated measured analysis of variance revealed a significant treatments effect ($P \leq 0.05$).

TABLE 1

Comparison of Brain Enzymatic Inactivation of Met-Enkephalin and Anodynin as Assessed by Opiate Receptor Binding Inhibition

| Incubation Conditions | % Inhibition Stereospecific Binding | |
|---|---|---|
| | Net-Enkephalin | Anodynin |
| Buffer—1 hr, 37° Particulate fraction | 65 | 29 |
| 1 hr, 0° | 65 | 29 |
| 0.25 hr, 37° | 39 | 18 |
| 1 hr, 37° | 2 | 18 |
| Supernatant fluid | | |

TABLE 1-continued

Comparison of Brain Enzymatic Inactivation of Met-Enkephalin and Anodynin as Assessed by Opiate Receptor Binding Inhibition

| Incubation Conditions | % Inhibition Stereospecific Binding | |
|---|---|---|
| | Net-Enkephalin | Anodynin |
| 1 hr, 37° | 1 | 20 |

Rat brains were homogenized in 100 volumes (wt/vol) of standard buffer and the particulate fraction and supernatant fluid were obtained by centrifugation for 10 min. at 40,000 × g. After incubation under the specified conditions in a total volume of 1 ml with met-enkephalin or anodynin, the samples were boiled for 2 min. and aliquots (300 $\mu$l) of the supernatant fluid were assessed forinhibition in the standard opiate receptor assay. The values are means from triplicate determinations of twoseparate experiments which varied less than 30%.

Orthogonal comparisons between the effects of anodynin and anodynin plus naloxone and morphine and morphine plus naloxone also proved to be significant (P $\leq$ 0.05). Both morphine and anodynin caused a stuperous immobility whose reversibility by naloxone was not assessed.

Effect of Hypophysectomy

Blood serum of rats whose pituitaries had been surgically removed 1 week previously was examined for opiate receptor inhibitory activity (see Table 2). While sham-operated control rats had opiate receptor inhibitory activity that was equivalent to 0.67 nmol of morphine per ml of plasma, levels in serum of hypophysectomized rats had fallen by 96–98%.

C. Discussion

Human blood contains a small (600 daltons) peptide with morphine-like behavioral and opiate receptor binding activity. This substance, anodynin, has been highly purified, as evidenced by the appearance of a single spot in three solvent systems for thin-layer chromatographic analysis. The ability to inhibit opiate receptor binding in vitro, as demonstrated by Pasternak, Goodman, and Snyder, "An Endogenous Morphine-like Factor in Mammalian Brain," *Life Science*, 16, 13–17, is a useful method for assessing purification progress.

TABLE 2

Levels of Anodynin in Rat Serum

| | No. of Rats | | % Inhibition of Stereospecific Binding | | Morphine Equivalence (nmol/ml) of Plasma) | |
|---|---|---|---|---|---|---|
| | Exp. 1 | Exp. 2 | Exp. 1 | Exp. 2 | Exp. 1 | Exp. 2 |
| Sham-operated Rats | 5 | 4 | 53±9 | 45±11 | 0.67 | 0.49 |
| Hypophysectomized Rats | 5 | 4 | 14±6 | 9±1 | 0.03 | 0.01 |

Butanol extracts of blood serum were prepared as in the Example (Materials and Methods) and aliquots from each sample (150 $\mu$l) were assayed for opiate receptor inhibition. Morphine inhibitory equivalence was calculated. The decrease in anodynin levels in hypophysectomized rats is significant (P <0.02).

We claim:

1. A method of recovering and purifying from human plasma an endogenous composition called anodynin having morphine agonist properties, which comprises acidifying said plasma to a pH of about 3.0 and heating said plasma, adjusting the pH to about 9.0 and recovering a precipitate, extracting said precipitate into butanol to recover anodynin from said butanol extract and reducing to dryness and subsequently purifying said anodynin by centrifuging and ion exchange column separation.

2. The method according to claim 1 wherein the composition having morphine agonist properties is further characterized by an apparent molecular weight of about 600.

3. The method according to claim 1 wherein the plasma is heated in a boiling water bath and the resulting fluid and precipitate are each extracted into butanol, subsequently the butanol extract is reduced to dryness and redissolved in a buffer at about pH 7.7 at 25° C, and subsequently undissolved material is removed by a low-speed centrifuge and purified in an ion exchange column.

* * * * *